United States Patent [19]

Childress et al.

[11] Patent Number: 5,489,701
[45] Date of Patent: * Feb. 6, 1996

[54] PROCESS FOR THE PREPARATION OF SILANE POLYSULFIDES

[75] Inventors: Thomas E. Childress, Newport; James S. Ritscher; Curtis L. Schilling, Jr., both of Marietta, all of Ohio; Okey G. Tucker, Jr., Vienna; Donald G. Beddow, Waverly, both of W. Va.

[73] Assignee: OSi Specialties, Inc., Danbury, Conn.

[ * ] Notice: The portion of the term of this patent subsequent to Nov. 14, 2012, has been disclaimed.

[21] Appl. No.: 383,480

[22] Filed: Feb. 2, 1995

Related U.S. Application Data

[63] Continuation-in-part of Ser. No. 314,204, Sep. 28, 1994.
[51] Int. Cl.$^6$ .................................................. C08F 7/08
[52] U.S. Cl. .................................... 556/427; 556/428
[58] Field of Search ................................ 556/427, 428

[56] References Cited

U.S. PATENT DOCUMENTS

| | | | |
|---|---|---|---|
| 3,842,111 | 10/1974 | Meyer-Simon et al. | 556/428 |
| 3,946,059 | 3/1976 | Janssen | 556/428 |
| 4,072,701 | 2/1978 | Pletka et al. | 556/428 |
| 4,129,585 | 12/1978 | Buder | 556/428 |
| 4,292,234 | 9/1981 | Borel | 556/427 |
| 4,507,490 | 3/1985 | Panster | 556/427 |
| 4,640,832 | 2/1987 | Bittner | 556/427 |
| 5,399,739 | 3/1995 | French et al. | 556/427 |
| 5,405,985 | 4/1995 | Parker et al. | 556/427 |

*Primary Examiner*—Mark D. Sweet
*Attorney, Agent, or Firm*—Andrew S. Reiskind

[57] ABSTRACT

Sulfur-containing organosilicon compounds useful as coupling agents in vulcanizable rubbers to enhance various properties, including low rolling resistance for automobile tires, are prepared. Preferred compounds include $\Omega,\Omega'$-bis (trialkoxysilylalkyl) polysulfides. The compounds are prepared by reacting sodium ethoxylate with hydrogen sulfide gas to yield a sodium sulfide solution, and then reacting this product with a slurried mixture of elemental sulfur and chloropropyltriethoxysilane to form the compound 3,3'-bis (triethoxysilylpropyl) tetrasulfide. The use of hydrogen sulfide gas and sodium metal alcoholates provides an efficient and economical process.

14 Claims, No Drawings

PROCESS FOR THE PREPARATION OF SILANE POLYSULFIDES

RELATED APPLICATION DATA

This application is a continuation-in-part of U.S. application Ser. No. 08/314,204, filed Sep. 28, 1994, which is incorporated herein in its entirety by reference.

TECHNICAL FIELD

The invention is directed to the preparation of sulfur-containing organosilicon compounds useful as coupling agents in vulcanizable rubbers to enhance products made from them. In its preferred form, the invention improves the preparation of $\Omega,\Omega'$-bis (trialkoxysilylalkyl) polysulfides.

Sulfur-containing organosilicon compounds have found widespread use in a variety of rubber products in the last two decades. Uses include tire walls and bodies, rubber hoses, rubber belts, and numerous other rubber products. Depending on the formulation, selected properties of the rubber can be modified.

Since the early 1980's, automobile manufacturers have been encouraging the production of low-rolling-resistance tires. A number of sulfur-containing organosilicon compounds have been identified as useful in this regard. The improvements obtainable could be helpful in meeting federal fuel economy standards without sacrificing wet traction and wear. Silane polysulfide coupling agents, such as 3,3'-bis (triethoxysilylpropyl) tetrasulfide, have been proposed for use in low-rolling-resistance tires.

To achieve optimum effect, it has been found that each low-rolling-resistance tire should contain several ounces of this or another suitable silane.

There is a need for new processes to produce organosilane polysulfides effective for use in low-rolling-resistance tires, and other uses, in good yield to permit economical production of large quantities with controllable safety and environmental impact.

BACKGROUND ART

The art of manufacturing organosilane polysulfides is well established, with the art offering a variety of processing strategies.

Meyer-Simon, Schwarze, Thurn, and Michel disclose the reaction of a metal polysulfide with an $\Omega$-chloroalkyltrialkoxysilane in U.S. Pat. No. 3,842,111. Example 2 shows the preparation of 3,3'-bis (triethoxysilylpropyl) tetrasulfide by reacting $Na_2S_4$ with 3-chloropropyltriethoxysilane in absolute ethanol. The procedure for preparing the metal polysulfide is not exemplified, and the examples imply that this starting material is an isolated compound.

In U.S. Pat. No. 4,072,701, Pletka describes the preparation of sulfur-containing organosilicon compounds by first heating 3-chloropropyltrichlorosilane (Example 1) with ethanol, and then adding both sulfur and NaSH in the presence of alcohol. The reaction developed gaseous hydrogen sulfide in situ, but some of the sulfur therein was not recoverable (see, U.S. Pat. No. 4,129,585, col. 1, lines 32–34, in this regard). Therefore, the yields based on added sulfur tended to be low. Also, the use of NaSH is problematic due to its deliquescent nature and its tendency to oxidize to sulfate. The deliquescence is troublesome from the standpoint that it increases the risk that water will enter the reaction and cause hydrolysis of the alkoxide reactants.

After describing the above two patents in U.S. Pat. No. 4,129,585, Buder, Pletka, Michel, Schwarz and Düsing, describe a procedure for making the noted compounds without the production of gaseous hydrogen sulfide. The process entails reacting a suitable alkali metal alcoholate, e.g., sodium ethoxide, in preferably alcoholic solution with a desired $\Omega$-chloroalkyltrialkoxysilane, a suitable metal hydrogen sulfide, and sulfur. The resulting product was purified by separating the salt formed and distilling off the alcohol. Again, the use of the metal hydrogen sulfide can be a source of water entering the system unless precautions are taken.

In U.S. Pat. No. 4,507,490, Panster, Michel, Kleinschmidt and Deschler, first prepare $Na_2S$. Again, they employ a metal hydrogen sulfide but react it with an alkali metal, such as sodium, in a polar solvent, such as ethanol. This reaction is highly exothermic and evolves hydrogen gas. The process is said to eliminate the use of an alkali metal alcoholate solution, noting that its production requires such a great deal of time as to be industrially improbable. The $Na_2S$ is reacted with additional sulfur to form a desired polysulfide, preferably $Na_2S_4$. The polysulfide is then reacted with a desired $\Omega$-chloroalkyl trialkoxysilane, e.g., $Cl(CH_2)_3Si(OC_2H_5)_3$, to form the desired $\Omega,\Omega'$-bis (trialkoxysilylalkyl) polysulfide.

Janssen and Steffen, in U.S. Pat. No. 3,946,059, offer a distinct approach and criticize procedures of the type described above. They eliminate the production, and therefore separation, of salts formed in the above reactions by contacting a bis (alkylalkoxysilyl) disulfide with sulfur at a temperature between 100° and 200° C. This procedure, however, adds the difficulty of the high temperature processing and requires the initial preparation of bis-silyl disulfides by the reaction of sulfuryl chloride with silyl mercaptans.

While the possibility might appear to exist that commercial forms of alkali metal sulfides, e.g., sodium tetrasulfide, could be employed, this would not be practical. The commercial forms of sodium tetrasulfide include water which must be completely removed prior to contact with the alkoxylates. If water is present, the alkoxide is hydrolyzed and a polysiloxane polymer is formed. And, while Bittner, et al. teach in U.S. Pat. No. 4,640,832, the reaction of sodium salts with hydrogen sulfide in alcoholic solution, this route has been criticized as "quite inconvenient" (see Lichty at CA, 7, 2910 (1913)).

Thus, the prior art has found the use of hydrogen sulfide gas, the separation of sodium chloride and the preparation of metal alkoxylates to be problematic in the preparation of sulfur-containing organosilicon compounds, and did not recognize that there was possible a reaction scheme which efficiently and effectively combines all of them. The invention provides a process which combines these and still obtains high yields based on sulfur.

SUMMARY OF THE INVENTION

It is an object of the invention to provide improved processes for preparing sulfur-containing organosilicon compounds useful as coupling agents in vulcanizable rubbers.

It is a further object of a preferred aspect of the invention to provide improved processes for preparing $\Omega,\Omega'$-bis (trialkoxysilylalkyl) polysulfides useful in the preparation of a variety of rubber products, specifically including low-rolling-resistance tires.

It is a further and more specific object of the invention to prepare 3,3'-bis (triethoxysilylpropyl)tetrasulfide economically in high yield.

These and other objects are achieved by the invention which provides a process for preparing silane polysulfides, comprising:

(a) contacting hydrogen sulfide gas with an active metal alkoxide solution; and then
(b) reacting the product of step (a) with a slurried mixture of elemental sulfur and a halohydrocarbylalkoxysilane of the formula

Q—R—X in which Q is

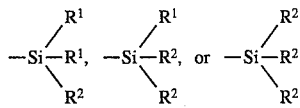

and in which $R^1$ is an alkyl group of 1 to 4 carbon atoms or phenyl, and $R^2$ is an alkoxy group with 1 to 8, preferably 1 to 4, carbon atoms,
  a cycloalkoxy group including 5 to 8 carbon atoms, or
  a straight or branched chain alkylmercapto group with 1 to 8 carbon atoms,
  wherein the various $R^1$ and $R^2$ groups can be the same or different, R is a divalent hydrocarbyl group including 1 to 18 carbon atoms, and X is a halogen, to produce a compound of the formula

Q—R—S—R—Q in which Q and R are as defined above, and n is an integer of from 2 to 9, preferably from 3 to 5.

The desired product is 3,3'-bis (triethoxysilylpropyl) tetrasulfide, represented by the formula $(C_2H_5O)_3Si(CH_2)_3$—$S_4$—$(CH_2)_3Si(OC_2H_5)_3$, and is prepared by a contacting an ethanol solution of sodium ethoxylate with hydrogen sulfide gas to produce a solution of sodium sulfide, and then reaction of the sodium sulfide so produced in a slurry with elemental sulfur and $Cl(CH_2)_3Si(OC_2H_5)_3$ and carrying the reaction to completion.

All parts and percentages in this description are on a weight basis and are based on the weight of the composition at the referenced stage of processing.

DETAILED DESCRIPTION

The invention, which relates to the preparation of sulfur-containing organosilicon compounds useful for a variety of purposes, especially as coupling agents in vulcanizable rubbers, will be described with special reference to the preparation of a preferred class of compounds, the Ω,Ω'-bis (trialkoxysilylalkyl) polysulfides.

Among this class of compounds are a large number of materials, including the various polysulfides listed below wherein the term polysulfide includes all of the di, tri, tetra, penta, hexa, hepta, octa, and nona-sulfides according to the following formulae:

bis (trimethoxysilylmethyl) polysulfides, bis (triethoxysilylmethyl) polysulfides, bis (dimethylethoxysilylmethyl) polysulfides, bis (tripropoxy-silylmethyl) polysulfides, bis (tributoxysilylmethyl) polysulfides, bis (tripentoxysilylmethyl) polysulfides, bis (trihexoxysilylmethyl) polysulfides, bis (triheptoxy-silylmethyl) polysulfides, and bis (trioctyloxysilylmethyl) polysulfides;

3,3'-bis (trimethoxysilylpropyl) polysulfides, 3,3'-bis (triethoxysilylpropyl) polysulfides, 3,3'-bis (dimethylethoxysilylpropyl) polysulfides, 3,3'-bis (tripropoxysilylpropyl) polysulfides, 3,3'-bis (tributoxysilylpropyl) polysulfides, 3,3'-bis (tripentoxysilylpropyl) polysulfides, 3,3'-bis (trihexoxysilylpropyl) polysulfides, 3,3'-bis (triheptoxysilylpropyl) polysulfides, 3,3'-bis (trioctyloxysilylpropyl) polysulfides, and 3,3'-bis (methyldiethoxysilylpropyl) polysulfides;

4,4'-bis (trimethoxysilylbutyl) polysulfides, 4,4'-bis (triethoxysilylbutyl) polysulfides, 4,4'-bis (dimethylethoxysilylbutyl) polysulfides, 4,4'-bis (tripropoxysilylbutyl) polysulfides, 4,4'-bis (tributoxysilylbutyl) polysulfides, 4,4'-bis (tripentoxysilylbutyl) polysulfides, 4,4'-bis (trihexoxysilylbutyl) polysulfides, 4,4'-bis (triheptoxysilylbutyl) polysulfides, and 4,4'-bis (trioctyloxysilylbutyl) polysulfides;

5,5'-bis (trimethoxysilylpentyl) polysulfides, 5,5'-bis (triethoxysilylpentyl) polysulfides, 5,5'-bis (dimethylethoxysilylpentyl) polysulfides, 5,5'-bis (tripropoxy-silylpentyl) polysulfides, 5,5'-bis (tripentoxysilylpentyl) polysulfides, 5,5'-bis (tripentoxysilylpentyl) polysulfides, 5,5'-bis (trihexoxysilylpentyl) polysulfides, and 5,5'-bis (triheptoxysilylpentyl) polysulfides, and 5,5'-bis (trioctyloxysilylpentyl) polysulfides.

Similarly, the 6,6'-bis (trialkoxysilylhexyl) polysulfides; the 7,7'-bis (trialkoxysilylheptyl) polysulfides; the 8,8'-bis (trialkoxysilyloctyl) polysulfides; the 9,9'-bis (trialkoxysilylnonyl) polysulfides; the 10,10'-bis (trialkoxysilyldecyl) polysulfides; and the isomers of these are included. Indeed, this disclosure is meant to include, each of the individual compounds comprised of combinations of the various groups encompassed by the generic formula

Q—R—S—R—Q wherein, Q, R and n are as defined above.

This description illustrates the production of the preferred compound, 3,3'-bis (triethoxysilylpropyl) tetrasulfide:

$(C_2H_5O)_3Si(CH_2)_3$—$S_4$—$(CH_2)_3Si(OC_2H_5)_3$ by the process described above. At times in the following description, Et is used to designate an ethyl group and Me is used to designate a methyl group.

Preparation of the Active Metal Alkoxide

As noted above, the process can be used to prepare a large number of end products. For each of these it is necessary to start with an active metal and an alcohol. They may be prereacted to form an active metal alkoxide solution. The active metal alkoxide will have the formula M-$R^2$, wherein M represents an active metal and $R^2$ is as defined above. Among the preferred active metals are those of the alkali metal group, especially sodium and potassium. The most preferred is sodium. However, among the other metals useful are lithium, rubidium and cesium. Among the preferred alkoxides are those containing methoxy, ethoxy, n-propoxy, i-propoxy, n-butoxy, i-butoxy, 2-methoxyethoxy or 2-ethoxyethoxy groups.

The prereaction, if performed, is carried out in a suitable organic solvent compatible with the alkoxide. In principle, any polar organic solvent can be employed that reacts with neither the alkali or other metal nor with the organic silicon compounds to form an undesired byproduct.

Preferably, the organic solvent is a linear or branched alcohol having 1 to 5 carbon atoms, e.g., methyl, ethyl, propyl, butyl or pentyl alcohol, as well as iso-propyl alcohol, iso-butyl alcohol and 2-methoxyethanol. Also suitable are cycloalkyl alcohols having 5 to 8 carbon atoms, e.g., cyclopentyl alcohol, cyclohexyl alcohol, cyclooctyl alcohol, phenyl or benzyl alcohol. It is useful to employ the alcohol which in each case corresponds to the $R^2$ group. In a given case, advantageously there can also be used a mixture of these alcohols, e.g., when different $R^2$ groups are used in a compound. Particularly preferred are methanol and ethanol, preferably in absolute form. In one preferred process, sodium metal is reacted with ethanol to form an ethanolic solution of sodium ethoxylate.

The reaction of active metal, e.g., sodium metal, and a suitable alcohol, e.g., ethanol, is preferably conducted with an excess of alcohol to produce a metal alkoxide, e.g., sodium ethoxide, solution. The following equation summarizes the reaction:

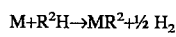

$$M + R^2H \rightarrow MR^2 + \tfrac{1}{2} H_2$$

The sodium or other metal should be maintained free of contact with moisture. The manufacture of sodium methoxide has been described by Arend (Arend, A. G., *Perfumery Essent. Oil Record*, 28, 372–75, 1947). The preferred sodium ethoxide reaction is similar to, but slower than, the sodium methoxide reaction.

The concentration of the sodium ethoxide solution may be as low as about 10 wt % and as high as its solubility limit, which is about 25 wt % at 25° C. A high concentration of sodium ethoxide is desirable, since better product yields for given reactor size are obtained. The typical concentration for commercially-available sodium ethoxide is about 21 wt %.

The H₂S-Active Metal Alkoxide Reaction

H₂S (hydrogen sulfide) gas is reacted with the active metal alkoxide (e.g., sodium ethoxide) in a suitable solvent (e.g., ethanol) to produce a suitable active metal sulfide, e.g., Na₂S:

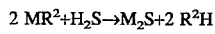

$$2\ MR^2 + H_2S \rightarrow M_2S + 2\ R^2H$$

This reaction can be performed in production quantities of from about 50 to about 5,000 pound batches. Continuous and semi-continuous processes can also be employed. Preferably, the reaction is carried out with an excess of ethanol, typically charging the preferred sodium ethoxide raw material as a 21 wt % solution in ethanol. The preferred reaction between hydrogen sulfide gas and sodium ethoxide employs a molar feed ratio of the hydrogen sulfide to the sodium ethoxide of 1:2.

The reaction is conveniently conducted in a semi-batch mode. First, all of the metal alkoxide is added to the reactor. Then, the reactor contents are heated to a temperature effective for reaction, in the preferred case discussed, within the range of from about 40° to about 50° C., e.g., about 50° C. The hydrogen sulfide gas is then fed to the reactor. The hydrogen sulfide feed rate is not critical, typically it will be of the order of one hour, but will vary with equipment and batch size. At the end of the reaction, most of the active metal sulfide is in solution. However, some solid active metal sulfide particles may be present. In general, it is desirable to keep the system agitated until the next step.

Preferably, the reactor is maintained at a temperature between about 40° and about 60° C. during the hydrogen sulfide addition to avoid discoloration. The reaction necessitates some degree of cooling. After the hydrogen sulfide addition is completed, it is desirable to purge out the feed conduit with nitrogen to prevent draw back of liquid. After the purge, the kettle is preferably cooled, e.g., to about 25° C., and then vented to atmospheric pressure through a reflux condenser to trap out any ethanol vapors while maintaining the kettle blanketed with nitrogen gas.

The system is preferably equipped with a scrubber or absorber for capturing hydrogen sulfide emissions. Strong sodium hydroxide is a good scrubbing medium. The reaction is preferably conducted in a mechanically-agitated kettle to assure good gas-liquid mixing to facilitate the reaction of the hydrogen sulfide with the active metal alkoxide. The hydrogen sulfide gas is desirably fed subnatantly via a diptube or gas sparger located near or preferably below the agitator.

Stoichiometry is important. The desired ratio is one mole of hydrogen sulfide per two moles of active metal alkoxide, with a preferred accuracy of hydrogen sulfide addition being about ±3%.

Sulfur and Halohydrocarbyltrialkoxysilane Addition and Reaction

The process of the invention employs a halohydrocarbyltrialkoxysilane for reaction with sulfur and the reaction product prepared above. These compounds meet the general formula Q—R—X in which Q and R are as defined above and X is a halogen, typically chlorine, but bromine, iodine and fluorine compounds can be effective. In this formula, and therefore also in the final product, the hydrocarbyl group R signifies methylene as well as preferably n-propylene, i-butylene, or n-butylene, but can also be n-pentylene, 2-methylbutylene, 3-methylbutylene, 1,3-dimethylpropylene, n-hexylene, or n-decylene.

Illustrative compounds within formula Q—R—X are 3-chloropropyltriethoxysilane, 3-bromopropyltriethoxysilane, chloromethyltrimethoxysilane, 3-chloropropyltrimethoxysilane, 3-chloropropyldiethoxymethylsilane, 3-chloropropylcyclohexoxydimethylsilane, 4-bromobutyldiethoxybenzylsilane, 4-chlorobutyltrimethoxysilane, 5-chloropentyldimethoxyphenylsilane, 3-bromo-i-butyltriethoxysilane, 3-chloropropyldimethoxy-p-ethylphenylsilane, 3-chloropropylethoxymethylethylsilane, 5-chloro-n-pentyldiethoxycyclopentylsilane, 3-bromopropyldimethoxycyclopentoxysilane, 3-bromo-2-methylpropyldimethoxy-cyclooctylsilane, 3-chloropropyldiethoxy-2-methoxyethoxy-silane, 3-chloropropyldibutoxymethylsilane, 3-bromopropylphenyloxydimethoxysilane, 3-chloropropyl-di-i-butoxy- 2-methylphenysilane, 4-chlorobutyldimethoxybenzyloxysilane, 3-chloropropyltributoxysilane, 3-chloropropyldiethoxyamylsilane, and 3-chloropropyldiethoxy-p-methylphenylsilane.

Again here, as in the case of the inclusion of compounds meeting the definition of the formula for the end products, this disclosure is meant to include each of the individual compounds comprised of combinations of the various groups encompassed by the generic formula Q—R—X in which R and X are as defined above.

Preferred chloroalkylalkoxysilanes can be purchased or prepared according to any of the techniques available to those of ordinary skill in the art. One preferred practice is to prepare it by transesterification of Cl(CH₂)₃Si(OMe)₃.

In an alternative embodiment of the invention, the methoxy ester can be employed to form 3,3'- bis (trimethoxyalkoxysilane) polysulfide, and this product can then be converted to the ethyl or higher ester by transesterification in situ.

According to this embodiment, Cl(CH₂)₃Si(OEt)₃ can be prepared by the following transesterification reaction, typically at a temperature of from about 70° to about 100° C. and atmospheric pressure using about 2000 ppm para-toluenesulfonic acid:

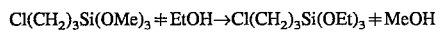

This reaction is preferably run by continuously feeding ethanol while removing by-product methanol from the system to drive the equilibrium toward chloropropyltriethoxysilane. The reaction can conveniently begin at atmospheric pressure and reflux temperatures, i.e., a pot temperature of from about 80° to about 100° C. At the end of the reaction, the excess ethanol can be stripped off using vacuum and a somewhat higher temperature. A typical final condition for the ethanol strip would be a temperature of about 120° C. and a pressure of about 100 mm Hg.

The active metal sulfide solution, e.g., product of the H₂S-active metal alkoxide reaction described above, is added to a slurry of elemental sulfur in the halohydrocarbylalkoxysilane. After the hydrogen sulfide addition and reaction is completed, the reaction mixture is cooled, e.g., to about 25° C., and the solution to is added to a slurry of S/Cl(CH₂)₃Si(OEt)₃ at around 40° to 45° C., until addition is complete, at a rate commensurate with the heat removal capability of the reactor. In laboratory glassware, this may require from about 1 to 3 hours. When the addition is complete, the reactor is preferably heated to about 80° C. and held at reflux for a suitable time, i.e., from about 1 to 3 hours, typically about 1.5 hours. It is preferred to maintain agitation in the reactor to insure solubilization and reaction, and to maintain in suspension the salt particles formed during the reaction. During this period, the system is preferably maintained at atmospheric pressure under a nitrogen blanket, to keep air out of the kettle to avoid oxidation which may contribute to a darkening of product color. After this reflux period, the reactor is immediately cooled, i.e., to about 25° C.

For the preferred product, the desired reaction is:

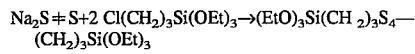

Salt Removal

The reaction produces the desired product and also produces salt. In the preferred reaction, sodium chloride salt produced in the sulfur and chloropropyl-triethoxysilane addition step can be removed by filtering or centrifuging. If filtration is used, the media pore size should be about 5μ. Typically, no filter aid is necessary since the average particle size is fairly large, but one can be employed if needed. If centrifuging is employed, a basket or continuous scroll-type device can be employed.

The resulting filtercake will contain residual liquid product and can be washed, e.g., with ethanol to improve overall product yield.

Solvent Strip

The process preferably includes a step of stripping off detrimental levels of solvent, preferably reducing the solvent concentration to less than about 5% by weight. In the preferred process as described above, assuming an ethanol wash has not been used, the crude product contains about 60 wt % ethanol. Stripping, preferably in a single stage, can be employed to yield a product containing less than about 2 wt % ethanol. One suitable stripping technique is batch stripping of the crude material in a reactor, e.g., to a final condition of 100° C. and 50 mm Hg absolute pressure. A small quantity of salt may precipitate out during the ethanol strip, and it is preferred to subject the product to a final filtration as necessary to remove this.

EXAMPLES

The following examples are presented for the purpose of further illustrating and explaining the invention, and are not to be taken as limiting in any regard. Unless otherwise indicated, all parts and percentages are based on the weight of the components at the indicated stage of processing.

Example 1

This example describes the preparation of the preferred end product, 3,3'- bis (triethoxysilylpropyl) tetrasulfide. To accomplish this result, sodium ethoxide was prepared fresh.

Preparation of Sodium Ethoxide

To a 500 ml glass reactor equipped with a feed funnel, a reflux column, a fritted glass sparge tube and thermometer, 17.0 grams of dry sodium chunks were added. Then, the reactor and the column were purged with N₂ for >5 minutes. Then, 227.4 grams of ethanol were charged into the feed funnel. During this step, the ethanol was added slowly enough to prevent the sodium from melting. After 85 minutes, all of the sodium was dissolved and the reactor was cooled from about 80° C. to about 40° C. for the next step.

H₂S Reaction with Sodium Ethoxide

Addition of hydrogen sulfide gas was started through a fritted glass sparge tube. The reaction was run with vigorous agitation during sparge. During a feed time of just under an hour, 12.7 grams of hydrogen sulfide gas was fed to the reactor. The solution was added to an addition funnel for later use.

Preparation of Chloropropyltriethoxysilane

Chloropropyltrimethoxysilane was separately transesterified to the ethyl ester, chloropropyltriethoxysilane, in a 1 liter glass reactor equipped with a heating mantle, thermometer, ethanol addition funnel and a 5 tray, 1 inch diameter glass Oldershaw column. This column should have at least about 3 theoretical trays.

The reactor was initially charged with 527.15 grams of chloropropyltrimethoxysilane, 1.05 grams of p-toluenesulfonic acid (2000ppm), and 130 grams of ethanol. During the first part of the reaction the reactor temperature was run in the range 80°–90° C. Then the ethanol feed rate was cut back and the reactor was run at 98°–115° C., to help drive MeOH out of the reactor. A reflux ratio of about 8:1 was used for the entire run. The ethanol usage was 2.3 times the theoretical amount. The reaction was run for about 8.9 hours, over a two day period. High temperature (111° C.) at the end of the run helped assure a relatively low residual ethanol concentration, i.e., 6.7%. This material could be vacuum stripped to reduce the ethanol further.

| PRODUCT ANALYSIS BY GAS CHROMATOGRAPHY | |
| --- | --- |
| Ethanol | 6.7 area % |
| Chloropropylmethoxydiethoxysilane | 1.02 area % |
| Chloropropyltriethoxysilane | 90.7 area % |

Reaction of Na$_2$S Solution with Sulfur/Chloropropyltriethoxysilane

The chloropropyltriethoxysilane made from transesterification of the corresponding methyl ester was used as the raw material to make 3,3'-bis (trialkoxysilylpropyl) tetrasulfide.

To a second glass reactor were added 184.6 grams chloropropyltriethoxysilane and 36.0 grams of ground sulfur. The reactor was equipped with a heating mantle, reflux column, agitator and thermometer. The silane-sulfur slurry was heated to 45° C. Then the Na$_2$S solution (contained in the addition funnel) was continuously added over a 2.3 hour period, during which the reaction temperature was maintained between 39° C. and 49° C. After the Na$_2$S addition was completed, the reaction was held at 45° C. for 1 hour, and then held at 75° C. for 1.5 hours.

Recovery of Product

The reactor was then cooled to room temperature. Its contents were filtered to remove NaCl solids formed in the reaction. Next the filtrate from the above step was stripped to 100° C. and 50 mm Hg to remove ethanol. Finally the stripped product was filtered through a 0.25 micron filter.

The final product had a weight of 190.6 grams. It was analyzed by gas chromatography (GC) and for % sulfur and shown to contain about 70% 3,3'-bis(triethoxysilylpropyl)tetrasulfide and about 25% 3,3'-bis(triethoxysilylpropyl) trisulfide at 22.4% contained sulfur. Less than 1% chloropropyltriethoxysilane was present. The gas chromatographic analysis was virtually identical to commercially available product and that produced by the process disclosed in U.S. application Ser. No. 08/314,204 cited above.

Example 2

Reaction of Na$_2$S/Chloropropyltriethoxysilane Product with Sulfur

This example illustrates the surprising results applicants achieve using the process of their invention as well as the importance of the ordered addition of reactants in applicants' claimed process.

In equipment analogous to that used above, a solution of Na$_2$S in ethanol was prepared as above from 260.7 grams of 21% sodium ethoxide in ethanol and 12.6 grams of H$_2$S gas. The solution was heated to reflux and 182.4 grams of chloropropyltriethoxysilane were added over a 1 hour period. After cooling to 25° C., 35.6 grams of sulfur were added, and heat applied to reflux within 30 minutes, followed by heating at reflux for 90 minutes. After filtration, gas chromatographic analysis of the unstripped product showed the major non-solvent component to be monosulfide, (EtO)$_3$Si(CH$_2$)$_3$S—(CH$_2$)$_3$Si(OEt)$_3$, with significant unreacted chloropropyltriethoxysilane. The unfiltered reaction mixture contained unreacted sulfur as well as the expected salt.

The above description is for the purpose of teaching the person of ordinary skill in the art how to practice the present invention and it is not intended to detail all of those obvious modifications and variations of it which will become apparent to the skilled worker upon reading the description. It is intended, however, that all such obvious modifications and variations be included within the scope of the present invention which is defined by the following claims. The claims cover the indicated components and steps in all arrangements and sequences which are effective to meet the objectives intended for the invention, unless the context specifically indicates the contrary.

We claim:

1. A process for the preparation of silane polysulfides comprising:

(a) contacting hydrogen sulfide gas with an active metal alkoxide solution, and (b) reacting elemental sulfur and a halohydrocarbylalkoxysilane of the formula Q—R—X with the product of step (a)

in which Q is

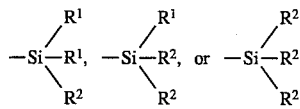

and in which

R$^1$ is an alkyl group of 1 to 4 carbon atoms or phenyl, and

R$^2$ is an alkoxy group with 1 to 8, preferably 1 to 4, carbon atoms,
      a cycloalkoxy group including 5 to 8 carbon atoms, or
      a straight or branched chain alkylmercapto group with 1 to 8 carbon atoms,
      wherein the various R$^1$ and R$^2$ groups can be the same or different, R is a divalent hydrocarbyl group including 1 to 18 carbon atoms, and X is a halogen, to produce a compound of of the formula Q—R—S$_n$—R—Q in which Q and R are as defined above, and n is an integer of from 2 to 9.

2. A process according to claim 1 wherein the product is purified to remove salt and solvent.

3. A process according to claim 1 wherein the products of the last reaction step are methoxy derivatives, and said methoxysilane derivatives are converted to silane derivatives containing higher alkoxy groups.

4. A process according to claim 1 wherein Q is

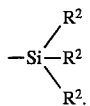

5. A process according to claim 1 wherein R$^2$ is ethoxy.

6. A process according to claim 1 wherein n is within the range of from 3 to 5.

7. A process according to claim 1 wherein the active metal alkoxide is sodium ethoxylate.

8. A process according to claim 1 wherein the halogen is chlorine.

9. A process according to claim 1 wherein R is 1,3-propylene.

10. A process for the preparation of $(C_2H_5O)_3Si(CH_2)_3$—$S_4$—$(CH_2)_3$ $Si(OC_2H_5)_3$, comprising:
  (a) contacting an ethanol solution of sodium ethoxylate with hydrogen sulfide gas to produce a solution of $Na_2S$, and
  (b) adding the solution of $Na_2S$ to an elemental sulfur and $Cl(CH_2)_3Si(C_2H_5O)_3$ slurry and reacting to completion.

11. A process according to claim 10 wherein the elemental sulfur and $Cl(CH_2)_3Si(C_2H_5O)_3$ slurry is formed by heating sulfur with $Cl(CH_2)_3Si(C_2H_5O)_3$.

12. A process according to claim 10 wherein sodium ethoxylate is formed by reacting sodium with ethanol.

13. A process according to claim 10 wherein salts formed in the reaction are filtered off and the solvents stipped off after the reaction is completed.

14. A process for the preparation of $(C_2H_5O)_3Si(CH_2)_3$—$S_4$—$(CH_2)_3$ $Si(OC_2H_5)_3$, comprising reacting sodium ethoxylate with hydrogen sulfide gas to yield a product and then reacting said product with a slurried mixture of elemental sulfur and $Cl(CH_2)_3Si(C_2H_5O)_3$.

* * * * *